United States Patent [19]

Walter, Jr. et al.

[11] Patent Number: 4,816,061

[45] Date of Patent: Mar. 28, 1989

[54] CONTROL OF BIOFOULING AT ALKALINE PH AND/OR HIGH WATER HARDNESS WITH CERTAIN ALKYLTHIOALKYLAMINES

[75] Inventors: Richard W. Walter, Jr.; Attila G. Relenyi, both of Midland, Mich.; Robert L. Johnson, Boise, Id.

[73] Assignee: The Dow Chemical Company, Midland, Mich.

[21] Appl. No.: 921,937

[22] Filed: Oct. 22, 1986

[51] Int. Cl.$^4$ .............................................. A01N 33/04
[52] U.S. Cl. ........................................ 71/67; 514/665
[58] Field of Search ...................... 71/67, 121; 514/665

[56] References Cited

U.S. PATENT DOCUMENTS

| | | | |
|---|---|---|---|
| 2,818,365 | 12/1957 | Deebel et al. | 167/22 |
| 3,291,683 | 12/1966 | Lamb | 167/22 |
| 3,524,719 | 8/1970 | Wolf et al. | 21/2.7 |

OTHER PUBLICATIONS

Komori et al., Yakagaku, vol. 20, (12), 887–90 (1971).

*Primary Examiner*—Catherine L. Mills
*Attorney, Agent, or Firm*—Craig E. Mixan; Ronald G. Brookens

[57] ABSTRACT

Disclosed is a method for inhibiting microorganisms and/or controlling biofouling of cooling towers by use of certain alkylthioalkylamines such as n-decylthioethylamine.

21 Claims, No Drawings

CONTROL OF BIOFOULING AT ALKALINE PH AND/OR HIGH WATER HARDNESS WITH CERTAIN ALKYLTHIOALKYLAMINES

BACKGROUND OF THE INVENTION

During the last 10 to 20 years, the methodologies employed for treating recirculating cooling tower systems have changed dramatically. Previous widely used methods for corrosion and deposit control involved the use of chromate based inhibitors plus an acid for scale control and not too much use of dispersants or antifoulants. The pH of the recirculating water was typically acidic and occasionally as high as neutral and the hardness of the water was relatively low due to the nature of the treatment and the few cycles of concentration (e.g., about 3). Such conditions resulted in comparatively low bioburden and biofouling. Good microbiological control was typically achieved by use of chlorine alone or in conjunction with certain nonoxidizing biocides to supplement the chlorine.

In more recent times the problem of biofouling of cooling tower systems has become much more severe due to the dramatic change in water treatment methodology. Nonchromate and chromate based on higher pH's are used as well as extensive use of dispersants. The pH of the recirculating water is much more alkaline and the hardness of the recirculating water has also increased due to the nature of the newer treatment and the substantially higher cycles of concentration typically employed (e.g., about 6-10).

The increase in the pH and hardness of the recirculating water has substantially reduced the effectiveness of chlorine and certain non-oxidizing biocides for controlling biofouling.

In addition, it is well known in the art that even subtle changes in a given environment can have a profound impact on the quality and quantity of any microflora present. Moreover, it is also well known that continuous use of a biocide will result in selections of organisms resistant to the biocide which can lead to ineffectiveness of that biocide over time.

For the above-noted reasons, it would be greatly desired to have a commercially acceptable method for controlling biofouling employing a biocide which is effective in inhibiting microorganisms at an alkaline pH and/or at high water hardness.

SUMMARY OF THE INVENTION

In its broadest aspect, the present invention is directed to a method for inhibiting microorganisms at an alkaline pH and/or at a high water hardness which comprises contacting said microorganisms with an effective amount of an alkylthioalkylamine compound of the formula

$$CH_3-(CH_2)_n-S-(CH_2)_m-NH_2 \qquad (I)$$

or the acid addition salts thereof, wherein
n is an integer of from 7 through 11, and
m is an integer of 2 or 3.

In another aspect, the present invention is directed to a method for controlling biofouling of a recirculating cooling tower system at an alkaline pH and/or at a high water hardness which comprises contacting said system with an effective amount of the alkylthioalkylamine compound of formula I.

Of the compounds of formula I for use in the present invention it is preferred that m is 2. It is also preferred that n is 9. The most preferred compound is n-decylthioethylamine.

As used herein the term "inhibit" or "inhibition" refers to suppression, control, kill or any other interference with the normal life processes of microorganisms that is adverse to the microorganisms; the term "alkaline pH" refers to any pH greater than 7; the term "high water hardness" refers to a hardness of greater than 100 ppm. For the purposes of the present invention "water hardness" has the same meaning as described in Microbiological Test Methods Compendium, First Edition, May, 1983, Chemical Specialties Manufacturers Association, 1001 Connecticut Avenue, N.W., Washington, D.C. 20036, incorporated herein by reference. Unless stated otherwise, as used herein hardness is expressed as parts per million (ppm) $CaCO_3$.

The term "effective amount" refers to that amount of one or more of the compounds of formula I needed to inhibit organisms. Typically, this amount varies from about 0.01 to about 5000 parts per million (ppm) by weight depending upon the specific industrial system conditions and the specific microorganism desired to be inhibited. A preferred effective amount is from about 0.1 to about 500 ppm, and a more preferred effective amount is from about 1 to about 50 ppm.

The term "biofouling" refers to slime formation, deposit formation, corrosion, discoloration, odor production or any other adverse consequences in industrial systems that are directly, indirectly or otherwise due to the presence or growth of microorganisms that are free in solution or are associated with a surface; the term "controlling biofouling" refers to prevention, reduction or elimination of biofouling.

DETAILED DESCRIPTION OF THE INVENTION

In the process of the present invention, the microorganisms that are inhibited are those microorganisms that are present or are capable of being present in industrial systems and are directly, indirectly or otherwise responsible for biofouling in industrial systems. Such microorganisms are planktonic or sessile and include bacteria, fungi and algae. A partial list, but by no means exhaustive list, of the organisms that are inhibited by the method of the present invention is as follows:

Bacillus subtilis, Pseudomonas aeruginosa, Enterobacter aerogenes, Escherichia coli, Proteus vulgaris, Staphylococcus aureus, Aspergillus niger, Candida albicans, Desulfovibrio desulfuricas, Actinomyces viscosus, Clostridium perfringens, Clostridium septicum, Bacteroides fragilis, Bacteroides multiacidus, Streptococcus faecalis, Streptococcus mutans, Lactobacillus casei, Streptococcus bovis, Fusobacterium necrophorum, Mucor michei, Erwinia amylovora, Salmonella typhimurium, Klebsiella pneumoniae, Sphaerotilus, Beggiatoa, Crenothrix, Aeromonas, Leptothrix, Pseudomonas putida, Pseudomonas fluorescens, Pseudomonas stutzeri, Pseudomonas cepacia, Zoogloea, Alcaligenes, Thiobacillus, Penicillium, Saccharomyces, Trichoderma, Aureobasidium, Chlorella, Volothrix, Anacystis, Anabaena, Oscillatoria, Diatoma, and Flagilaria.

Industrial systems that have the requisite alkaline pH and/or high hardness include, but are not limited to, cooling towers, paper mills, paint and paint films, cosmetics, and metalworking fluids. Preferred is cooling towers.

In the process of the present invention, it is preferred that the pH of the industrial system is between about 7.5 and about 12 and a more preferred range is between about 8 and about 9.5. It is preferred that the water hardness is between about 150 ppm and about 2,000 ppm and more preferred that the hardness is between about 300 ppm and about 1,500 ppm.

Methods for the preparation of the alkylthioalkylamine compounds of formula I are known in the art, for example, in U.S. Pat. Nos. 3,291,363 and 3,524,719, incorporated herein by reference. For instance these materials can be prepared by the reaction of thioalkylamine with an alcohol of the necessary chain length. They can also be prepared by reacting ethyl oxazoline with a mercaptan and then hydrolyzing the resulting product to remove propionic acid.

The acid addition salts of the alkylthioalkylamine compounds of formula I can be conveniently prepared by methods known in the art, e.g., by acidifying with a suitable acid such as HCl, HBr, $H_3PO_4$, $HNO_3$, $H_2SO_4$ or other mineral acids; or weaker acid such as acetic, propionic, butyric, glycolic, or other monofunctional or polyfunctional carboxylic acid to obtain the acid addition salt corresponding to the particular alkylthioalkylamine and acid employed. It is contemplated that mixtures of acids and/or alkylthioalkylamines can be employed to obtain the corresponding mixture of the acid addition salts. The hydrochloride salts of the alkylthioalkylamine compounds of formula I are preferred.

Although a variety of biocides are used in industrial systems, it has been found that certain biocides that are effective at one pH can be ineffective at other pH's. Furthermore, for many types of biocides the pH response is totally unpredictable.

Heretofore, standard procedures for determining antimicrobial activity typically used in the art are performed at about neutral pH. Reliance upon efficacy determination of biocides at neutral pH can be partially or totally misplaced when such biocide is to be applied to an industrial system at an alkaline pH. In order to arrive at the process of the present invention, an improved assay wherein the microbial inhibitory activity of compounds at alkaline pH is determined has been developed to allow determination of pH effects on agar based bioefficacy determinations.

It is contemplated that the compounds of formula I can be applied to industrial systems at alkaline pH and/or at high hardness in the form of compositions. The composition, in addition to one or more of the compounds of formula I, can contain inert ingredients, antimicrobial adjuvants, or other active ingredients. The exact concentration of one or more of the alkylthioalkylamine compounds of formula I to be employed in the treating compositions is not critical to bioefficacy but may be critical to end use formulations and may vary considerably provided that an effective amount is capable of being supplied to the industrial system. The concentration of said alkylthioalkylamine compounds in liquid compositions generally is from about 0.00001 to about 15 percent by weight; however, concentrations up to 45 percent by weight may be employed. In solid or dust compositions, the concentrations of the alkylthioalkylamine compounds can be from about 0.0001 to about 98 percent by weight.

In compositions to be employed as concentrates, the alkylthioalkylamine compounds can be present in a concentration of from about 0.01 to about 98 percent by weight.

In the preparation of dust compositions, one or more of the alkylthioalkylamine compounds of formula I can be admixed with any of the finely divided solids, such as pyrophyllite, talc, chalk, gypsum and the like. In such operations, the finely divided carrier is ground or mixed with the said compounds or wet with a solution of the compounds in a volatile organic solvent. Similarly, dust compositions containing the products can be prepared using various solid surface active dispersing agents such as fuller's earth, bentonite, attapulgite and other clays. Depending upon the proportions of ingredients, these dust compositions can be employed for the control of pests or employed as concentrates and subsequently diluted with an additional solid surface active dispersing agent or with pyrophyllite, chalk, talc, gypsum and the like to obtain the desired amount of active ingredient in a composition adapted to be employed as described herein. Also, such dust compositions when employed as concentrates can be dispersed in water, with or without the aid of dispersing agents to form spray mixtures.

Further, spray compositions can be prepared by incorporating one or more of the alkylthioalkylamine compounds of formula I, or their liquid or dust concentrate compositions, in mixtures with surface-active dispersing agents such as an ionic or non-ionic emulsifying agent. Such spray compositions are readily employed for the control of microbes or are dispersed in liquid carriers to form diluted sprays containing the compounds in any desired amount suitable for microbial control. The choice of dispersing agents and amounts thereof employed are determined by the ability of the agents to facilitate the dispersion of the concentrate in the liquid carrier to produce the desired spray compositions.

Similarly, the alkylthioalkylamine compounds of formula I can be admixed with a suitable water-immiscible organic liquid and a surface-active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Suitable organic liquids which can be employed in the composition include petroleum oils and distillates, toluene, liquid halohydrocarbons and synthetic organic oils. The surface-active dispersing agents are usually employed in liquid compositions in the amount of from about 0.1 to about 10 to about 20 percent by weight of the combined weight of the dispersing agent and active compound.

In addition, other liquid compositions containing the desired amount of one or more of the alkylthioalkylamine compounds of formula I can be prepared by dissolving said compounds in an organic liquid such as acetone, methylene chloride, chlorobenzene and petroleum distillates. The preferred organic solvent carriers are those which are adapted to accomplish the penetration and impregnation of the environment to be treated.

In further embodiments, the compounds as employed in accordance with the present invention, or compositions containing the same, can be advantageously employed in the methods described herein in combination with one or more pesticidal or preservative compounds. In such embodiment, such pesticidal or preservative compound is employed either as a supplemental active constituent, an additament or as an adjuvant. Representative pesticidal or preservative compounds include the substituted phenols, cresols, substituted cresols and their metal salts, the bisphenols and thiobisphenols, the halogenated salicylanilides, the organosulfur compounds, the carbamate compounds, the quaternary ammonium compounds, the organometallic compounds, the inorganic salts and miscellaneous other compounds.

For treating a recirculating cooling water system, it is preferred that one or more of the alkylthioalkylamine compounds of formula I is incorporated into said system by means of a slug dose pumped on a daily to weekly basis. It is also preferred that the resulting concentration of the alkylthioalkylamine compound in the recirculating cooling water is from about 0.1 to about 100 ppm by weight. Such treatment conditions typically result in good to excellent control of biofouling in the cooling tower system.

The following examples are to further illustrate the present invention but should not be interpreted as a limitation thereon.

EXAMPLE 1

The media used for the various methods described herein are listed below.

| Ingredient | Amount |
| --- | --- |
| NUTRIENT BROTH | |
| Difco Nutrient Broth | 0.8 gram (g) |
| Deionized Water | 1.0 liter (l) |
| NUTRIENT AGAR | |
| Difco Nutrient Agar | 23.0 g |
| Deionized Water | 1.0 l |
| MALT YEAST AGAR | |
| Difco Malt Agar | 45.0 g |
| Difco Yeast Extract | 3.0 g |
| Deionized Water | 1.0 l |

EXAMPLE 2

Minimum Inhibitory Concentration (MIC) Procedure

The agar (nutrient agar) was dispensed in 30 ml aliquots into 25×200 millimeter (mm) test tubes, capped and autoclaved for 15 minutes at 115° C. The test tubes containing the agar were cooled in a water bath until the temperature of the agar was 48° C. and then an appropriate amount of the one percent solution of the test compound was added (except in the controls where no test compound was added) to the respective test tubes so that final concentrations of 500, 250, 100, 50, 25, 10, 5, 2.5, 1.0 and 0 parts per million (ppm) of the test compound in the agar were obtained. The agar solutions were each mixed and poured into individual petri plates so that each petri plate contained agar having a known concentration of test compound dispersed therein. After drying for 24 hours, the petri plates were inoculated with bacteria.

The inoculation with bacteria was accomplished using the following procedure. Twenty-four hour cultures of the bacteria were prepared by incubating the bacteria in tubes containing nutrient broth for 24 hours at 30° C. in a shaker. Dilutions of the 24 hour culture were made so that a suspension was made, containing about $10^8$ colony forming units (CFU) per ml of suspension of bacteria. Aliquots of 0.3 ml of the above suspension were used to fill individual wells of a Steer's Replicator. The Steer's Replicator was then used to inoculate the petri plates.

The petri plates were incubated at 30° C. for 48 hours and then read to determine if the test compound which was incorporated into the agar prevented growth of the respective bacteria. The minimum inhibitory concentration (MIC) for each bacteria was defined as the lowest concentration of the test compound which prevented growth of that bacteria.

EXAMPLE 3

Kill Time Evaluation

Materials and Methods

Hard water was prepared by sterilizing deionized water and adjusted to 500 ppm hardness and 100 ppm alkalinity by addition of 16.7 ml of sterile $CaCl_2.2H_2O$ (36.8 g/l), 16.7 ml of sterile $MgSO_4.7H_2O$ (12 g/l), and 5 ml of sterile $NaHCO_3$ (16.8 g/l) to 1 liter of water. The pH was adjusted by addition of diluted NaOH or acetic acid.

Kill Time Procedure

Nutrient broth containing 300 ppm total organic carbon (TOC) and 800 ppm total dissolved solids (TDS), was adjusted to pH 8.5 with NaOH and dispensed in 10 ml aliquots into 18×150 mm test tubes. These tubes were capped and autoclaved for 15 minutes at 121° C. Immediately before use, 50 microliters ($\mu l$) of a heat sterilized solution of 31.74 g/l $MgCl_2$ and 73.99 g/l $CaCl_2$ was added to tubes designated to contain 500 ppm hardness. The tubes with and without added hardness were readjusted to pH 8.5 by addition of appropriate amounts of a filter sterilized solution of 16.8 g/l NaHCO. One hundred and eighty and 125 $\mu l$ of the NaHCO solution were added, respectively, to tubes with and without added hardness to achieve a pH of 8.5.

Unless otherwise indicated, *Enterobacter aerogenes*, ATCC #13048, was used as the test organism. Three 0.1 ml aliquots of a 24 hour nutrient broth culture were pipetted onto three nutrient agar plates and spread uniformly with a Petri dish spreader. After 24 hours' growth, the cells were scraped and washed off the agar surface with sterile glass rods (hockey sticks) and sterile saline solution. After vigorous mixing (vortexing) to break up clumps, the cell suspension was filtered through a sterile filter (Whatman #4) to remove residual clumps. The resultant cell suspension was subsequently diluted with sterile saline to give 1:100 dilutions which resulted in an optical density (O.D.) at 550 nanometers (nm) of 0.06 (Bausch & Lomb Spectronic 710 equipped with a flow thru cell). Solutions with this optical density, when diluted 1:100, contained approximately $10^{10}$ CFU/ml when plated on standard nutrient agar. The exact number of organisms was determined by making serial dilutions of the cell suspension and plating them on nutrient agar plates. Each of the serial dilution tubes was also streaked on a nutrient agar plate. These streaks of known concentrations of organisms were then used as controls to determine the number of organisms in the test samples.

Just prior to the addition of the test compounds, 0.1 ml of the cell suspension containing approximately $10^{10}$ cells/ml was added to the prepared broth tubes. Solutions of 0.1 percent weight/weight (w/w) of experimental compound were prepared immediately before use. Appropriate amounts of these solutions were added to achieve final concentrations of 100, 50, 25, 10, 5 ppm of active ingredient in broth tubes both with and/or without hardness. The tubes were then incubated at 30°

C. After three and/or 24 hours, dilutions of the broth tubes were made by addition of 0.1 ml of the broth into 9.9 ml of 0.85 percent saline containing 100 ppm NaHSO₃. From the saline tube the samples were streaked with cotton swabs onto nutrient agar plates which also contained 100 ppm NaHSO₃.

The plates were incubated for 24 hours and then read. The number of organisms present in the broth tubes was determined by comparing these plates to the control plates of the serial dilution tubes.

EXAMPLE 4

Effect of pH on Kill Time Activity of n-decylthioethylamine (DTEA) Against *Enterobacter aerogenes*

Dilute (1/10) nutrient broth was prepared according to standard methods known in the art and then adjusted to a variety of pH's by the addition of NaOH and HCl. The Kill Time Procedure substantially similar to that described in Example 3 was performed. High water hardness was not evaluated in this study. The results of this procedure were as follows.

| Concentration (ppm) of DTEA That Kills all Cells in 3 Hours at Various pH's | | | | | | | |
|---|---|---|---|---|---|---|---|
| pH | 5 | 6 | 7 | 8 | 9 | 10 | 11 | 12 |
| ppm | 50 | 50 | 20 | 10 | 5 | ≦5 | ≦5 | ≦5 |

EXAMPLE 5

Effect of Chain Length on Kill Time Activity

The Kill Time Evaluation substantially similar to that described in Example 3 was performed. The results were as follows:

| | | | ppm of the Compound that Killed all Cells | | | | |
|---|---|---|---|---|---|---|---|
| Time | pH | (ppm CaCO₃) | n-hexylthio-ethylamine* | n-octylthio-ethylamine | n-decylthio-ethylamine | n-dodecylthio-ethylamine | n-tetradecyl-thioethylamine |
| 3 hr | 8.5 | 500 | 500 | 150 | 20 | 50 | >500 |
| 24 hr | 8.5 | 500 | 250 | 75 | 40 | 150 | >500 |

Test for hardness:
Bausch & Lomb test kit for total hardness which measures both Ca and MgCO₃ hardness as ppm CaCo₃.
*Not an example of the present invention

EXAMPLE 6

Effect of Chain Length on MIC of Certain alkylthioalkylamines Against *Enterobacter aerogenes* at Alkaline pH The MIC procedure substantially as described in Example 2 was performed. High water hardness was not evaluated in this study. The results were as follows:

| Compound | MIC at pH 8.2 |
|---|---|
| n-hexylthioethylamine* | 250–500 |
| n-octylthioethylamine | 25 |
| n-nonylthioethylamine | 25 |
| n-decylthioethylamine | 10–25 |
| n-undecylthioethylamine | 50 |
| n-dodecylthioethylamine | 50–100 |
| n-tetradecylthioethylamine* | >500 |

*Not an example of the present invention

EXAMPLE 7

The kill time procedure substantially as described in Example 3 was performed using *Aspergillus niger* at a pH of 8.2 to 8.3. Malt yeast agar was used instead of nutrient agar and the incubation times were extended to accommodate the slower growing fungi cells. The results are as follows.

| | Ppm of Compound that Resulted in Kill of All Cells at Various Times | | |
|---|---|---|---|
| Compound | 3 hr. | 6 hr. | 24 hr. |
| n-octylthioethylamine | 50 | 25 | 10 |
| n-decylthioethylamine | 3.5 | 0.5–3.5 | 0.1 |

What is claimed is:

1. A method for inhibiting microorganisms at an alkaline pH and at a high water hardness which comprises contacting said microorganisms with an effective amount of n-decylthioethylamine or the acid addition salts thereof.

2. The method of claim 1 carried out in an industrial system selected from the group consisting of a cooling tower, a paper mill, a paint or paint film, a cosmetic, and a metalworking fluid.

3. The method of claim 1 wherein said alkaline pH is between about 7.5 and about 12 and said high water hardness is between about 150 ppm and about 2,000 ppm.

4. The method of claim 1 wherein said alkaline pH is between about 8 and about 9.5 and said water hardness is between about 300 ppm and about 1,500 ppm.

5. A method for inhibiting microorganisms at a high water hardness which comprises contacting said microorganisms with an effective amount of n-decylthioethylamine or the acid addition salts thereof.

6. The method of claim 5 carried out in an industrial system selected from the group consisting of a cooling tower, a paper mill, a paint or paint film, a cosmetic, and a metalworking fluid.

7. The method of claim 5 wherein said high water hardness is between about 150 ppm and about 2,000 ppm.

8. The method of claim 5 wherein said high water hardness is between about 300 ppm and about 1,500 ppm.

9. A method for inhibiting microorganisms at an alkaline pH which comprises contacting said microorganisms with an effective amount of n-decylthioethylamine or the acid addition salts thereof.

10. The method of claim 9 carried out in an industrial system selected from the group consisting of a cooling tower, a paper mill, a paint or paint film, a cosmetic, and a metalworking fluid.

11. The method of claim 9 wherein said alkaline pH is between about 7.5 and about 12.

12. The method of claim 9 wherein said alkaline pH is between about 8 and about 9.5.

13. A method for controlling biofouling of a recirculation cooling tower system at an alkaline pH and at a high water hardness which comprises contacting said microorganisms with an effective amount of n-decylthioethylamine or the acid addition salts thereof.

14. The method of claim 13 wherein said alkaline pH is between about 7.5 and about 12 and said high water hardness is between about 150 ppm and about 2,000 ppm.

15. The method of claim 13 wherein said alkaline pH is between about 8 and about 9.5 and said water hardness is between about 300 ppm and about 1,500 ppm.

16. A method for controlling biofouling of a recirculating cooling tower system at a high water hardness which comprises contacting said microorganisms with an effective amount of n-decylthioethylamine or the acid addition salts thereof.

17. The method of claim 16 wherein said high water hardness is between about 150 ppm and about 2,000 ppm.

18. The method of claim 16 wherein said high water hardness is between about 300 ppm and about 1,500 ppm.

19. A method for controlling biofouling of a recirculating cooling tower system at an alkaline pH which comprises contacting said microorganisms with an effective amount of n-decylthioethylamine or the acid addition salts thereof.

20. The method of claim 19 wherein said alkaline pH is between about 7.5 and about 12.

21. The method of claim 19 wherein said alkaline pH is between about 8 and about 9.5.

* * * * *